US008703104B2

(12) United States Patent  
Morelli et al.

(10) Patent No.: US 8,703,104 B2
(45) Date of Patent: Apr. 22, 2014

(54) USE OF METAL ASTRINGENTS FOR THE TREATMENT OF HAIRY HEEL WARTS

(75) Inventors: Joseph P. Morelli, Bothell, WA (US); Jeffrey R. Fernandes, Port Orchard, WA (US); Edward L. C. Verkaar, LW Amstelveen (NL); Petra Vogt, St. Paul, MN (US)

(73) Assignee: Ecolab USA Inc, St. Paul, MN (US)

( * ) Notice: Subject to any disclaimer, the term of this patent is extended or adjusted under 35 U.S.C. 154(b) by 1439 days.

(21) Appl. No.: 11/977,613

(22) Filed: Oct. 25, 2007

(65) Prior Publication Data

US 2009/0110645 A1    Apr. 30, 2009

(51) Int. Cl.
*A61K 9/12* (2006.01)
*A61K 33/06* (2006.01)
*A61K 31/00* (2006.01)

(52) U.S. Cl.
USPC .............................. 424/43; 424/682; 424/685

(58) Field of Classification Search
None
See application file for complete search history.

(56) References Cited

U.S. PATENT DOCUMENTS

| 2,824,042 | A | 2/1958 | Gibbons et al. |
| 3,061,512 | A | 10/1962 | Anderson, Jr. et al. |
| 3,265,571 | A | 8/1966 | Krezanoski et al. |
| 3,856,941 | A | 12/1974 | Turner |
| 4,034,750 | A | 7/1977 | Seiderman |
| 4,073,887 | A | 2/1978 | McLean, Sr. |
| 4,268,504 | A | 5/1981 | Harrington et al. |
| 4,284,611 | A | 8/1981 | Gancy et al. |
| 4,362,643 | A | 12/1982 | Kuo et al. |
| 4,388,308 | A | 6/1983 | Hamilton et al. |
| 4,537,767 | A | 8/1985 | Rothman et al. |
| 4,551,100 | A | 11/1985 | Fischer |

(Continued)

FOREIGN PATENT DOCUMENTS

| GB | 2250196 | 6/1992 |
| WO | WO00/57703 | 10/2000 |
| WO | WO02/060433 | 8/2002 |
| WO | WO02/072076 | 9/2002 |

OTHER PUBLICATIONS

Laven et al. (The Veterinary Journal 22006, 171, 79-88).*

(Continued)

*Primary Examiner* — Ernst Arnold
*Assistant Examiner* — Jianfeng Song
(74) *Attorney, Agent, or Firm* — Amy J. Hoffman; Andrew D. Sorensen

(57) ABSTRACT

A system and method for treating hoof related diseases, particularly hairy heel warts (papillomatus digital dermatitis), includes an aqueous solution having a metal astringent at a therapeutically effective concentration. The metal astringent includes aluminum, iron, and mixtures thereof. In preferred embodiments, the metal may include a mixture of monomeric and polymeric species. The polymeric species may be in the form of a polymeric concentrate, such as, for example, polyaluminum chloride or polyferric sulfate. Alternatively, the polymeric species may be formed by partially neutralizing a metal salt. The aqueous solution of the metal astringent is applied to a lower leg and hoof area of an animal using any known application technique, including, but not limited to, foot baths, foams and spray applications. In preferred embodiments, the aqueous solution is applied using an automated dispensing system. The aqueous solution may include additional components, such as surfactants and thickeners, to enhance the performance of the metal astringent or contribute additional functionality.

24 Claims, 2 Drawing Sheets

(56) References Cited

U.S. PATENT DOCUMENTS

| | | | |
|---|---|---|---|
| 4,563,342 | A | 1/1986 | Gunnarsson et al. |
| 4,840,798 | A | 6/1989 | Skaliotis |
| 4,879,116 | A | 11/1989 | Fox et al. |
| 4,895,517 | A | 1/1990 | Fischer |
| 4,945,084 | A | 7/1990 | Packman |
| 5,182,094 | A | 1/1993 | Kvant et al. |
| 5,246,686 | A | 9/1993 | Cuer et al. |
| 5,250,569 | A | 10/1993 | Godfrey |
| 5,348,721 | A | 9/1994 | Murphy et al. |
| 5,575,995 | A | 11/1996 | Giovanoni |
| 5,630,379 | A | 5/1997 | Gerk et al. |
| 5,653,994 | A | 8/1997 | Schneider et al. |
| 5,772,985 | A | 6/1998 | Kemp et al. |
| 5,780,064 | A | 7/1998 | Meisters et al. |
| 5,785,862 | A | 7/1998 | Graham et al. |
| 5,916,447 | A | 6/1999 | Hultén et al. |
| 5,985,234 | A | 11/1999 | Dulko |
| 6,028,104 | A | 2/2000 | Schmidt et al. |
| 6,036,935 | A | 3/2000 | Dulko |
| 6,162,429 | A | 12/2000 | Wallis et al. |
| 6,168,794 | B1 | 1/2001 | Reusser et al. |
| 6,382,136 | B1 | 5/2002 | Bragulla et al. |
| 6,444,707 | B1 | 9/2002 | Lampe et al. |
| 6,451,341 | B1 | 9/2002 | Slaga et al. |
| 6,458,391 | B1 | 10/2002 | Reusser et al. |
| 6,479,058 | B1 | 11/2002 | McCadden |
| 6,530,343 | B1 | 3/2003 | Lind |
| 6,596,325 | B1 | 7/2003 | Vroom |
| 6,630,434 | B2 | 10/2003 | Besse et al. |
| 6,652,840 | B1 | 11/2003 | Prevendar |
| 6,797,260 | B1 | 9/2004 | Prevendar |
| 6,803,056 | B2 | 10/2004 | Dolak |
| 6,863,898 | B2 | 3/2005 | Clawson |
| 6,884,412 | B1 | 4/2005 | Wallis et al. |
| 7,097,861 | B1 | 8/2006 | O'Brien |
| 2002/0102314 | A1 | 8/2002 | Watson |
| 2002/0169476 | A1 | 11/2002 | Cohen |
| 2003/0077304 | A1 | 4/2003 | McCadden |
| 2003/0190355 | A1 | 10/2003 | Hermelin et al. |
| 2003/0232086 | A1 | 12/2003 | McCadden |
| 2004/0037899 | A1 | 2/2004 | Ryan et al. |
| 2004/0053799 | A1 | 3/2004 | Collin |
| 2004/0175433 | A1 | 9/2004 | Thomson |
| 2005/0053672 | A1 | 3/2005 | West |
| 2005/0123620 | A1 | 6/2005 | Chiou |
| 2005/0186288 | A1 | 8/2005 | Chiou et al. |
| 2005/0191366 | A1 | 9/2005 | McCadden |

OTHER PUBLICATIONS

Activon, "*New Foaming Hoof Cleanser System*", www.activon.com, Oct. 3, 2006, 1 page.

Casey, William H., "*Large Aqueous Aluminum Hydroxide Molecules*", Chemical Reviews, vol. 106, No. 1, 2005, 16 pages.

Kofler, J, Pospichal, M., Hofmann-Parisot, M., "*Efficacy of the Non-antibiotic Paste Protexin® Hoof-Care for Topical Treatment of Digital Dermatitis in Dairy Cows*", J. Vet. Med. A 51, 447-452 (2004).

Marabo, "*Mint with Natural Marigold Dynamint Udder Cream*", www.marabo.com, Oct. 3, 2006, 1 page.

Marabo, "*SuperCharger Intensifier and Activator*", http://www.marabo.com, Oct. 3, 2006, 2 pages.

Parthasarathy, N., Buffle, J., "*Study of Polymeric Aluminium(III) Hydroxide Solutions for Application in Waste Water Treatment. Properties of the Polymer and Optimal Conditions of Preparation*", Water Res. vol. 19, pp. 25-36, 1985, 12 pages.

Petplace, "*Burow's Solution*", 2007, http://www.petplace.com, 3 pages.

Protexin, "Hoof Care for Horses", 2006, http://www.protexin.com, 1 page.

Roullier, "*PODOCUR SV*", www.roullier.com, Oct. 3, 2006, 1 page.

Westagro, "*Double Action™—Hoof Treatment Concentrate*", http://www.westagro.com, Oct. 3, 2006, 8 pages.

WestfaliaSurge, "*PediCuRx Hygiene Products*", http://www.westfalia.com, Oct. 3, 2006, 2 pages.

Laven, R. A., et al., "Treatment strategies for digitial dermatitis for the UK," The Veterinary Journal, 171, pp. 79-88 (2006).

Supplementary European Search Report mailed Dec. 21, 2011.

Novartis, "Digital Dermatitis Q&A", Nov. 22, 2004.

Anonymous, "Aluminum Acetate Topical Solution (Domeboro, Bluboro, Burow's Solution)", Operational Medicine 2001.

Hilary M. Sullivan, "Hairy Foot Wars", Mar. 2005.

\* cited by examiner

USE OF METAL ASTRINGENTS FOR THE TREATMENT OF HAIRY HEEL WARTS

BACKGROUND

The present invention relates to the treatment and prevention of foot disease in cattle and other types of hoofed animals. More particularly, the present invention relates to the use of metal astringents for the treatment and prevention of hairy heel wart disease.

Hairy heel wart disease, also known as Papillomatus Digital Dermatitis (PDD), Digital Dermatitis (DD), strawberry heel warts, or Mortellaro disease, is an infectious disease transmitted among hoofed animals. The disease is manifested as painful skin lesions that form near the junction of the skin and hoof area. In the progressed state, the lesions can produce long hair-like skin growths (papilliforms). The effects of the disease include lameness, loss of weight and decline of general well-being. In the case of dairy cattle, the disease results in a loss of milk production. In some cases, interventive surgery may be required to protect the life of the animal. The disease etiology is recognized as a multivariate problem involving environmental, managerial, and bacterial factors. Exposure to high levels of moisture and manure is likely a significant factor to the disease. In addition, the rapid response to topical antibiotics indicates a bacteriological factor, and Treponema spirochaete has been observed in lesions linked to hairy heel wart disease.

Treatment practices for dairy cattle may vary tremendously from farm to farm. Most farms, particularly large dairy operations, may treat the cows multiple times per week to help prevent new cases of hairy heel warts and treat existing infections. Common prophylactic treatments include copper sulfate or formaldehyde with copper sulfate.

Foot baths are commonly used to apply the copper sulfate. After the cows are milked, they are directed to walk through troughs containing a solution of copper sulfate. As more cows move through a foot bath, the trough may become filled with so much soil and organic waste that active components in the foot bath become ineffective, and the trough may even become a vehicle for transferring bacteria between cows. Thus, the foot baths require a significant labor commitment as the solution in the foot bath may need to be replaced frequently. Moreover, these types of foot baths result in high volumes of copper sulfate waste, and in some cases, formaldehyde waste. Copper sulfate is becoming more expensive and the associated environmental concerns continue to increase. There is a need for a system and method of effectively treating and preventing hairy heel wart disease that eliminates the use of copper sulfate, while simultaneously reducing material costs and labor costs.

SUMMARY

A system and method for treating hoof related diseases, particularly hairy heel warts (papillomatus digital dermatitis), includes an aqueous solution having a metal astringent at a therapeutically effective concentration. The metal astringent includes aluminum, iron, and mixtures thereof. In preferred embodiments, the metal may include a mixture of monomeric and polymeric species. The polymeric species may be in the form of a polymeric concentrate, such as, for example, polyaluminum chloride or polyferric sulfate. Alternatively, the polymeric species may be formed by partially neutralizing a metal salt. The aqueous solution of the metal astringent is applied to a lower leg and hoof area of an animal using any known application technique, including, but not limited to, foot baths, foams and spray applications. In preferred embodiments, the aqueous solution is applied using an automated dispensing system. The aqueous solution may include additional components, such as surfactants and thickeners, to enhance the performance of the metal astringent or contribute additional functionality.

DETAILED DESCRIPTION

Figure 1:
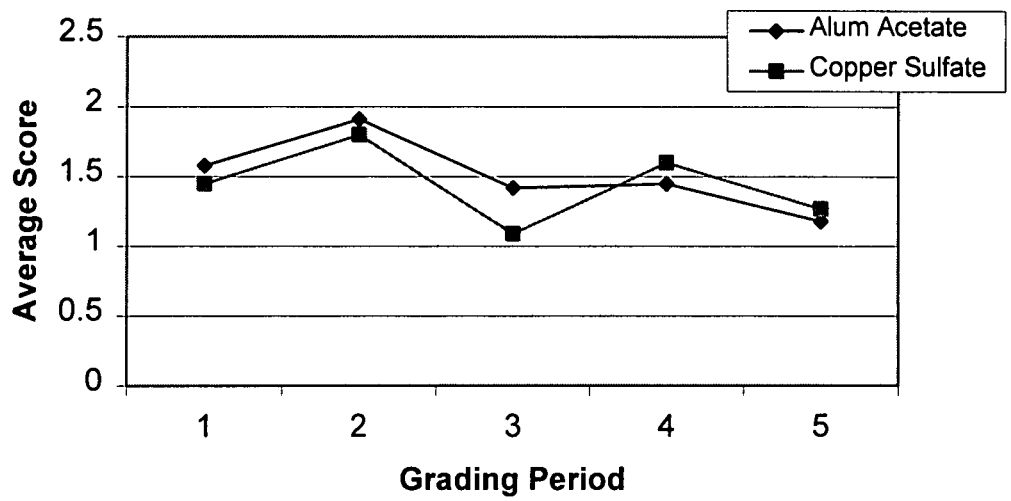
FIG. 1 is a plot of an average score of lesion size for a group of cows during a herd study to compare an aluminum acetate treatment to a copper sulfate treatment.

A system and method is described herein for treating and preventing hoof related diseases in cows and other hoofed animals or ungulates, including sheep, pigs and horses. The system includes an aqueous solution having an astringent metal salt, such as aluminum and/or iron, which is present in a therapeutically effective amount in the aqueous solution. Under some conditions, the astringent metal may form a mixture of polymeric and monomeric species. As illustrated below, an aqueous solution having a lower concentration of an aluminum astringent, as compared to a more concentrated copper treatment, achieved comparable results in retarding the progression of hairy wart disease. While not wanting to be bound by theory, it is believed that the polymeric aluminum species improves an astringent impact of the metal. A treatment that uses a lower concentration of the metal astringent is more economical and less hazardous to the environment. Moreover, as described below, an automated system may be used to apply the treatment, which reduces labor costs.

Astringent agents promote a precipitation of proteins on a skin's surface and may be used to stop or slow down bleeding and promote drying out of lesions. This disclosure focuses on trivalent metal ion astringents, particularly aluminum and iron, for the treatment and prevention of hairy heel wart disease. The polycationic metal ions likely promote cross linking and precipitation of proteins through ionic interactions. This cross linking may toughen the skin against the macerating effects of moisture and manure that may be the prelude to new infections, as well as promote the drying up and inactivation of existing lesions. Thus, the chemistry of these metal ions is well-suited for both the treatment and prevention of hairy heel wart disease. In preferred embodiments, the astringent metals comprise salts in which the metal ion and the corresponding ligand are only weakly associated in the aqueous solution. Metal hydrates form that can then be partially neutralized to form metal hydroxide poloxocations with high polycationic states.

The metal astringent agents are derived from aluminum, iron and combinations of aluminum and iron. Aluminum astringent agents include, but are not limited to, aluminum behenate, aluminum benzoate, aluminum bromohydrate, aluminum chloride, aluminum chlorohydrate (also known as polyaluminum chloride), aluminum dichlorohydrate, aluminum sesquichlorohydrate, aluminum hydroxide, aluminum citrate, aluminum formate, aluminum glycolate, aluminum glycinate, aluminum lactate, aluminum nitrate, aluminum phosphate, sodium aluminum phosphate, aluminum propionate, aluminum subpropionate, aluminum stearate, aluminum sulfate, ammonium, potassium aluminum sulfate, sodium aluminum sulfate, aluminum acetate (Burow's solution), aluminum subacetate, aluminum chlorohydrex polyethylene glycol, aluminum chlorohydrex propylene glycol, aluminum dichlorohydrex polyethylene glycol, aluminum dichlorohydrex propylene glycol, aluminum sesquichloroghydrex polyethylene glycol, aluminum sesquichlorohydrex propylene glycol, aluminum zirconium octachlorohydrate, aluminum zirconium octachlorohydrex gly, aluminum zirconium pentachlorohydrate, aluminum zirconium pentachlorhydrex gly, aluminum zirconium tetrachlorohydrate, aluminum zirconium tetrachlorhydrex gly, aluminum zirconium trichlorhydrate, aluminum trichlorohydrex gly, polyaluminum sulfate, polyaluminum sulfate chloride, polyaluminum ferrisulfate, polyaluminum ferrisulfate chloride, polyaluminum ferrichloride, polyaluminum sulfate silicate, and mixtures thereof.

As stated above, it is preferred to use an aluminum agent where the ligand (for example, chloride) weakly binds to the metal when the astringent is in an aqueous solution. Preferred aluminum astringent agents include, but are not limited to, aluminum chloride, aluminum sulfate, sodium aluminum sulfate, potassium aluminum sulfate, aluminum acetate, aluminum subacetate, aluminum lactate, or any polyaluminum species. Aqueous concentrates of aluminum sulfate and various polyaluminum salts are commonly used in the water treatment industry and are commercially available.

Iron astringent agents include, but are not limited to, ferric chloride, ferric ammonium citrate, ferric ammonium sulfate, ferric sulfate, ferric subsulfate (Monsel's solution), ferric citrate, ferric lactate, ferric nitrate, ferric orthophosphate, ferric phosphate, ferric pyrophosphate, ferric tartrate, polyferric chloride, polyferric sulfate, and mixtures thereof. Preferred iron astringent agents include, but are not limited to, ferric chloride, ferric sulfate, ferric subsulfate, polyferric chloride, polyferric sulfate, and mixtures thereof.

An appropriate concentration of the metal content in the aqueous solution is between approximately 0.01 and 1.5 weight percent. Another measure that may be used to quantify the metal in the aqueous solution is the concentration of the astringent agent (i.e. the metal and the ligand that it binds to; for example, aluminum acetate or aluminum sulfate). An appropriate concentration of the metal astringent in the aqueous solution is between approximately 0.01 and 10 weight percent, and a preferred concentration is between approximately 0.1 and 5.0 weight percent. As an example, in the herd study described below, an aqueous solution containing 0.56 weight percent of aluminum acetate was tested; the aluminum content was approximately 0.07 weight percent. For purposes of this disclosure, the concentration of the metal in the aqueous solution is generally described in terms of the weight percent of the metal content. As described below, in preferred embodiments, the aqueous solution is prepared by diluting a concentrate of the metal astringent. The concentrate may be in the form of a powder, a tablet, dispersion or liquid.

In some embodiments, the metal astringent in the aqueous solution is a mixture of monomeric and polymeric species. (The polymeric species also may be referred to as polynuclear or metal hydroxide poloxocations.) Reference is made to Casey, W. H., *Large Aqueous Aluminum Hydroxide Molecules*, Chemical Reviews, 2005, vol. 106, pp. 1-16 for additional background on polymeric species. In aqueous solutions, aluminum may form hydrates and polyaluminum species. These polyaluminum species, such as polyaluminum chloride, polyaluminum sulfate, and polyaluminum chlorosulfate, are used for water treatment in order to provide the greatest efficiency to coagulate and settle out suspended materials in drinking water. These highly cationic complexes may also promote greater protein precipitation due to a greater number of ionic sites for interaction. These polymeric systems comprise a plurality of polymer species depending on the manufacturing process and an age of the polymeric system. The system may include well characterized species such as, for example, $Al_{13}^{7+}$ tridecamer $Al_{12}(OH)_{24}AlO_4(H_2O)_{12}^{+7}$ and $Al_{30}^{18+}$ ($Al_2O_8Al_{28}(OH)_{56}(H_2O)_{26}^{+18}$), which are identifiable using techniques such as nuclear magnetic resonance spectroscopy and x-ray crystallography.

In one embodiment, the polyaluminum species may be formed by increasing the pH and partially neutralizing an aqueous solution of an aluminum salt. Increasing the basicity of the aqueous solution results in a greater percentage of the polyaluminum species. However, if the conditions of the aqueous solution are too basic, poorly soluble aluminum hydroxide is formed. In a preferred embodiment, a pH level of the aqueous solution is between 4.0 and 6.0, in order to maximize a percentage of polyaluminum species in the aqueous solution.

The most commonly recognized aluminum astringents are aluminum sulfate and aluminum acetate. Aluminum acetate is reported in the Code of Federal Regulations as being an astringent active ingredient at concentrations ranging between 0.13 and 0.5 percent, whereas aluminum sulfate is reported at concentrations of 46 to 63 percent. (See 21 C.F.R. 347.) As such, aluminum acetate (i.e. Burow's solution) likely has a greater weight efficiency than aluminum sulfate. While not wishing to be bound by theory, it is believed that aluminum acetate may more easily form these polyaluminum species, compared to aluminum sulfate, and thus a lower concentration of aluminum acetate may be sufficient as an astringent. However, it is recognized that aluminum sulfate, at certain conditions, may also form polyaluminum species.

Partially neutralized solutions of aluminum may be described and classified by the molar ratio of hydroxide [OH] and aluminum [Al] (i.e. R is equal to [OH]/[Al]). For purposes here, a maximum value of R is generally less than three since at R equal to three a precipitate of $Al(OH)_3$ forms. A suitable range of R is between approximately 0.2 and 2.7, in order to maintain an aqueous solution, and a preferred range of R is between approximately 1.0 and 2.5. At these ratios, at least some of the aluminum species in the aqueous solution is polymeric or polynuclear.

Many polyaluminum products may be described by an R value and/or a basicity percentage [(R/3)*100%]. For example, a coagulant of polyaluminum chloride used in the water treatment industry has a basicity of approximately 83-84 percent and an R value of approximately 2.49-2.52. An alternative composition of polyaluminum chloride has a basicity of approximately 50 percent and an R value equal to approximately 1.5. Similarly, a coagulant of polyaluminum chlorosulfate has a basicity of approximately 50 percent and an R value of approximately 1.5.

An aqueous solution containing polyaluminum may be formed using at least two different methods. In one embodiment, a polyaluminum concentrate, such as, for example, polyaluminum chloride (aluminum chlorohydrate), may be diluted to form an aqueous solution of polyaluminum. In an alternative embodiment, as described above, an aluminum salt may be diluted and combined with an alkalinity source to form the polyaluminum species in situ. Reference is made to U.S. Pat. No. 5,348,721 and U.S. Pat. No. 5,985,234, both of which disclose the formation of polyaluminum chlorosulfates for use in water treatment. Also see U.S. Pat. No. 4,284,611 and U.S. Pat. No. 6,036,935 for additional background on the formation of polyaluminum solutions.

Similar to aluminum, iron may also form a mixture of monomeric and polymeric species in an aqueous solution, under certain conditions. Commercially available coagulants used in drinking water include polyferric chloride and polyferric sulfate. As also described above for aluminum, a polyferric species may be formed by partially neutralizing a ferric salt. See U.S. Pat. No. 5,785,862 and U.S. Pat. No. 5,916,447, which both describe the formation of polymeric iron for the water treatment industry.

Solutions of iron may also be classified by the molar ratio of hydroxide [OH] and iron (i.e. R is equal to [OH]/[Fe]). A suitable R range for aqueous solutions containing iron is between approximately 0.1 and 0.5, and a preferred value is approximately 0.3. As stated above, an example of a commercially available product is polyferric sulfate having an R value of 0.3 and a basicity of approximately 10 percent.

An aqueous solution also may be a mixture of polyaluminum, polyferric species, and poly-alumino-ferric species.

In most cases, the metal astringent in an aqueous solution is a mixture of monomeric and polymeric species. The quantification of aluminum and iron species can be measured using the standard ferron assay. For example, three classes of aluminum species, $Al_a$ for monomeric aluminum, $Al_b$ for medium sized polyaluminum species, and $Al_c$ for large polyaluminum species, are quantified based on the reaction time with the ferron dye. The ferron dye is believed to react rapidly and irreversibly with the monomeric metal, whereas polymeric forms of the metal take longer to react depending on their size. The standard convention is to quantify $Al_a$ (monomeric aluminum) by the reaction that occurs in the initial 3 minutes, $Al_b$ (medium sized polymeric species) by the reaction that occurs between 3 minutes and 30 minutes, and $Al_c$ (large polymeric species) by the difference between the total aluminum content and $Al_a+Al_b$. Reference is made to D. R. Parker, P. M. Bertsch, *Identification and Quantification of the $Al_{13}$ Tridecamer Polycation Using Ferron*, Environ. Sci. Technol. 1992, vol. 26, pp. 908-914 for additional background on using the ferron assay for speciation of a metal. For our purposes, polyaluminum is defined by $Al_b$ and $Al_c$. Other techniques that may be used to classify the speciation of the metal include nuclear magnetic resonance spectroscopy, size exclusion chromatography, and x-ray crystallography. Total aluminum content can be determined by atomic adsorption or inductively coupled plasma. Reference is made to Standard Methods for the Examination of Water and Wastewater 20th Edition, ed. Clesceri L. S., Greenberg A. E., Eaton A. D. American Public Health Association, 1998, Washington D.C.

In some embodiments, aluminum and iron may be used in combination in an aqueous solution, and both the aluminum and the iron may form polymeric species. The pH of the aqueous solution is preferably between approximately 4.0 and 6.0 to optimize formation of the polyaluminum and polyferric species, which are believed to be a significant contributor to the astringent affect of the metals. The aqueous solution may be classified based on a weight percent of the aluminum and/or iron that is in polymeric form, based on results from the ferron assay. A suitable amount of the polymeric species, which includes aluminum, iron and mixtures thereof, is equal to or greater than approximately 10 weight percent of the total metal in the solution. A preferred range of the polymeric species is between approximately 25 and 95 weight percent of the total metal, and more preferably between approximately 50 and 95 weight percent.

Herd Study

A study was conducted to compare the results of treating cows with copper sulfate and with aluminum acetate. Treatment A was an aqueous solution of copper sulfate at 4.0 weight percent. A pre-weighed sample containing 19.7-19.8 grams of copper sulfate pentahydrate (98%, ACS Grade, Sigma Aldrich) was combined with 16 ounces of potable water to form the solution of copper sulfate. Treatment B was an aqueous solution of aluminum acetate at 0.56 weight percent, and a pH of approximately 4.1. The concentration of the aluminum content was 0.07 weight percent. Pre-weighed samples containing 10.1-11.5 grams of Domeboro Astringent Solution Powder from Bayer were dissolved in 16 ounces of water to produce the aqueous solution for treatment B. Each packet of Domeboro Astringent Powder contained 839 mg calcium acetate, 1191 mg aluminum sulfate, and dextran. The calcium acetate and aluminum sulfate reacted to form aluminum acetate and calcium sulfate. The calcium sulfate precipitated from the solution and all of the composition (the aqueous solution and the precipitate) was applied as described below.

The study was performed at a commercial dairy farm having approximately 450 Holstein cows. The cows were housed in free stalls with sawdust bedding, milked three times daily, and fed a total mixed ration. Prior to this study using treatments A and B, the cows were treated with a copper sulfate or formaldehyde foot bath once a week and non-responsive lesions were bandaged with a tetracycline bandage.

Prior to the start of applying treatments A and B, cows with similar lesions (i.e. size and colorations) were paired together and randomly assigned to one of the two treatment groups. A minimum of ten cows was included in each group.

Treatments A and B were applied to the lesions on the cows using hand sprayers (i.e. 32 oz spray bottles). The study lasted for twenty days, with the last treatment being applied on the seventeenth day and the last scoring observation on the twentieth day. The five measured attributes included lesion size, lesion color, lesion appearance, lesion pain, and locomotion. The scoring for each measure is shown in Table 1 below.

TABLE 1

| Observation Scoring | |
| --- | --- |
| Lesion Size | 0 = No |
| | 1 = Dime Size |
| | 2 = Quarter Size |
| | 3 = Half Dollar Size |
| Color | 0 - No Lesion |
| | 1 - Bright Red |
| | 2 - Dark Red |
| | 3 - Dark Red/Grayish Black |
| | 4 - Very Dark Black |
| | 5 - Normal skin color with a small inverted horseshoe band of white or black tissue |
| Appearance | 1 - Moist granular with no hair like projections |
| | 2 - granulated tissue with white hair like projections and some moistness |
| | 3 - Significant dry granulation and hair like projections around edge and possibly in the middle |
| | 4 - Dead lesion with drying crusty dehydrated tissue |
| | 5 - No lesion to thin black scab |
| Pain | 0 - No pain |
| | 1 - Minor pain raised leg <2s |
| | 2 - Major pain raised leg >2s |
| Locomotion | 1 - Stands and walks normal with level back |
| | 2 - Stands with flat back but arches when walks, slightly abnormal gait |
| | 3 - Stands and walks with arched back, abnormal gait with short strides in one or more feet |
| | 4 - Arched back standing and walking with one or more feet that can still bear some weight |

TABLE 1-continued

Observation Scoring

5 - Severely lame, reluctant to move or bear weight on one or more feet

Based on the scoring in Table 1, an objective of the study was to determine the number of cows that, at the end of the study, showed a change to an inactive lesion color (i.e. score greater than or equal to 4), minor or no lesion pain, and at least the same size lesion or smaller as compared to the beginning of the study. A comparison between Treatment A (copper sulfate) and Treatment B (aluminum acetate) was based on the proportions of cows showing a disappearance of lesions, inactivation of lesions, and a comparison of average lesion size between only those cows having inactive color scores.

Table 2 below shows which days the treatments were applied to the lesions and which days (i.e. grading period) the attributes from Table 1 were measured.

TABLE 2

Study Schedule

| Day | Treatment Number | Grading Period |
|---|---|---|
| 0 | | 1 |
| 1 | 1 | |
| 3 | 2 | |
| 5 | 3 | 2 |
| 7 | 4 | |
| 9 | 5 | |
| 10 | | 3 |
| 12 | 6 | |
| 14 | 7 | 4 |
| 16 | 8 | |
| 19 | | 5 |

The treatments began on Day 1, and were applied every two or three days. The attributes were measured at five different grading periods, with grading period 1 at day 0, which was one day prior to application of the first treatment. A table is included for each of the five measurable attributes in Table 1, showing the scoring at each of the grading periods. (A corresponding graph is also included.) Some cows were not graded at all grading periods. The reported sums in the tables below reflect this. Average scores in the tables were based on the number of cows graded at each grading period.

Table 3 shows the scoring for the lesion size on a scale of 0 to 3. The distribution of the scores at each grading period is shown, as well as the average lesion size. The average scores are plotted in FIG. 1.

TABLE 3

Lesion Size Score Distribution

| | Grading Period | | | | |
|---|---|---|---|---|---|
| Grade Score | 1 (Day 0) | 2 (Day 5) | 3 (Day 10) | 4 (Day 14) | 5 (Day 19) |
| Aluminum | | | | | |
| 0 | 0 | 0 | 0 | 0 | 0 |
| 1 | 6 | 3 | 7 | 6 | 9 |
| 2 | 5 | 6 | 5 | 5 | 2 |
| 3 | 1 | 2 | 0 | 0 | 0 |

TABLE 3-continued

Lesion Size Score Distribution

| | Grading Period | | | | |
|---|---|---|---|---|---|
| Grade Score | 1 (Day 0) | 2 (Day 5) | 3 (Day 10) | 4 (Day 14) | 5 (Day 19) |
| CuSO4 | | | | | |
| 0 | 0 | 0 | 0 | 0 | 0 |
| 1 | 6 | 4 | 10 | 4 | 8 |
| 2 | 5 | 4 | 1 | 6 | 3 |
| 3 | 0 | 2 | 0 | 0 | 0 |
| Average Al | 1.58 | 1.91 | 1.42 | 1.45 | 1.18 |
| Average CuSO4 | 1.45 | 1.80 | 1.09 | 1.60 | 1.27 |
| Sum Al | 12 | 11 | 12 | 11 | 11 |
| Sum CuSO4 | 11 | 10 | 11 | 10 | 11 |

By grading period 5 (day 19), 9 out of 11 cows undergoing treatment with aluminum acetate had a lesion size of 1, as compared to 8 out of 11 cows undergoing treatment with copper sulfate. However, none of the lesions disappeared entirely within the study period.

Figure 2:
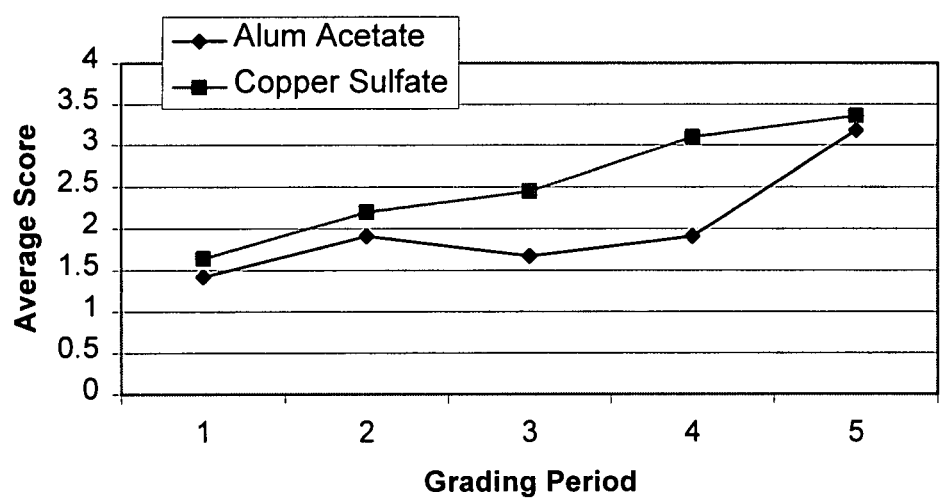
FIG. 2 is a plot of average scores of lesion color during the herd study of FIG. 1.

Table 4 and FIG. 2 show the scoring distribution and average scores for the lesion color on a scale of 0 to 5.

TABLE 4

Lesion Color Score Distribution

| | Grading Period | | | | |
|---|---|---|---|---|---|
| Grade Score | 1 (Day 0) | 2 (Day 5) | 3 (Day 10) | 4 (Day 14) | 5 (Day 19) |
| Aluminum | | | | | |
| 0 | 0 | 0 | 0 | 0 | 0 |
| 1 | 9 | 5 | 6 | 6 | 1 |
| 2 | 1 | 2 | 4 | 2 | 1 |
| 3 | 2 | 4 | 2 | 2 | 5 |
| 4 | 0 | 0 | 0 | 0 | 3 |
| 5 | 0 | 0 | 0 | 1 | 1 |
| CuSO4 | | | | | |
| 0 | 0 | 0 | 0 | 0 | 0 |
| 1 | 6 | 2 | 1 | 2 | 0 |
| 2 | 3 | 5 | 5 | 0 | 2 |
| 3 | 2 | 2 | 4 | 3 | 5 |
| 4 | 0 | 1 | 1 | 5 | 2 |
| 5 | 0 | 0 | 0 | 0 | 2 |
| Average Al | 1.42 | 1.91 | 1.67 | 1.91 | 3.18 |
| Average CuSO4 | 1.64 | 2.20 | 2.45 | 3.10 | 3.36 |
| Sum Al | 12 | 11 | 12 | 11 | 11 |
| Sum CuSO4 | 11 | 10 | 11 | 10 | 11 |

A lesion having a color score of 4 and above is designated as an inactive lesion. In the group treated with aluminum acetate, 4 out of 11 cows changed to an inactive lesion by day 19. The same results were observed in the group treated with copper sulfate. As shown in FIG. 2, the aluminum acetate appeared to take longer to inactivate the lesion; however, the average score for aluminum acetate increased significantly between grading periods 4 and 5 such that the averages at day 19 were comparable between the two treatment groups.

Figure 3:
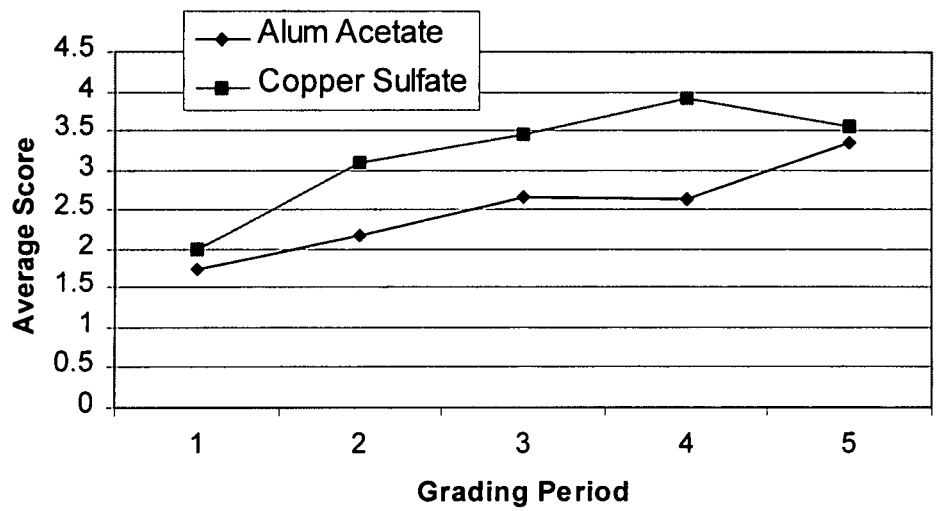
FIG. 3 is a plot of average scores of lesion appearance during the herd study.

Table 5 and FIG. 3 are directed to measuring the appearance of the lesion, particularly moistness, on a scale of 1-5.

TABLE 5

Lesion Appearance Score Distribution

| | Grading Period | | | | |
|---|---|---|---|---|---|
| Grade Score | 1 (Day 0) | 2 (Day 5) | 3 (Day 10) | 4 (Day 14) | 5 (Day 19) |
| Aluminum | | | | | |
| 1 | 6 | 3 | 2 | 1 | 0 |
| 2 | 4 | 3 | 3 | 5 | 2 |
| 3 | 1 | 5 | 4 | 3 | 4 |
| 4 | 1 | 0 | 3 | 1 | 4 |
| 5 | 0 | 0 | 0 | 1 | 1 |
| CuSO4 | | | | | |
| 1 | 4 | 0 | 0 | 0 | 0 |
| 2 | 4 | 4 | 1 | 0 | 1 |
| 3 | 2 | 1 | 4 | 3 | 5 |
| 4 | 1 | 5 | 6 | 5 | 3 |
| 5 | 0 | 0 | 0 | 2 | 2 |
| Average Al | 1.75 | 2.18 | 2.67 | 2.64 | 3.36 |
| Average CuSO4 | 2.00 | 3.10 | 3.45 | 3.90 | 3.55 |
| Sum Al | 12 | 11 | 12 | 11 | 11 |
| Sum CuSO4 | 11 | 10 | 11 | 10 | 11 |

As shown in Table 5 and FIG. 3, there was a disparity between the results of the two treatments between grading periods 2 and 4. Specifically, those lesions treated with the copper sulfate appeared to be "drying up" quicker than those treated with the aluminum acetate. However, at grading period 5, the average scores (3.36 for aluminum acetate and 3.55 for copper sulfate) were comparable. As shown in Table 5, five out of 11 cows treated with aluminum acetate received a score of 4 or 5; similarly, five out of 11 cows treated with copper sulfate received a score of 4 or 5.

Figure 4:
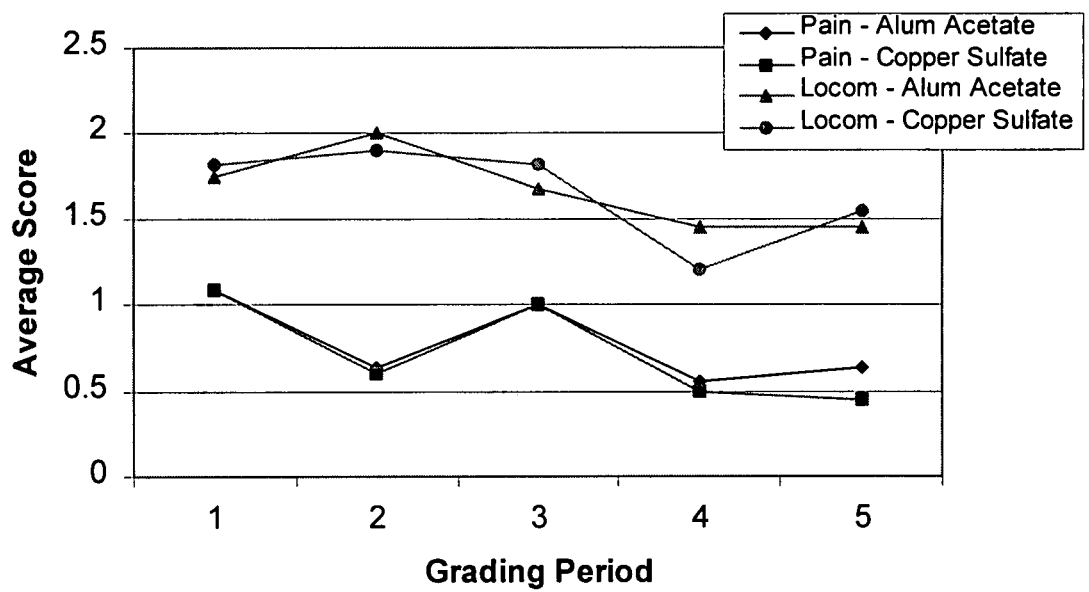
FIG. 4 is a plot of averages scores of pain and locomotion during the herd study.

Lesion pain is quantified in Table 6 and FIG. 4, based on a score between 0 and 2. Lesion pain was the first of the five attributes measured at each of the grading periods. At the beginning of the observation process, the hooves of the cows were cleaned with water to remove debris in order to make the lesion more visible. Lesion pain was measured based on each cow's response to the cleaning process (i.e. did the cow raise its leg(s) and for how long).

TABLE 6

Lesion Pain Score Distribution

| | Grading Period | | | | |
|---|---|---|---|---|---|
| Grade Score | 1 (Day 0) | 2 (Day 5) | 3 (Day 10) | 4 (Day 14) | 5 (Day 19) |
| Alluminum | | | | | |
| 0 | 0 | 4 | 1 | 5 | 4 |
| 1 | 11 | 7 | 10 | 6 | 7 |
| 2 | 1 | 0 | 1 | 0 | 0 |
| CuSO4 | | | | | |
| 0 | 0 | 4 | 1 | 5 | 6 |
| 1 | 10 | 6 | 9 | 5 | 5 |
| 2 | 1 | 0 | 1 | 0 | 0 |
| Average Al | 1.08 | 0.64 | 1.00 | 0.55 | 0.64 |
| Average CuSO4 | 1.09 | 0.60 | 1.00 | 0.50 | 0.45 |
| Sum Al | 12 | 11 | 12 | 11 | 11 |
| Sum CuSO4 | 11 | 10 | 11 | 10 | 11 |

Prior to beginning treatment, all but one of the cows in each of the treatment groups exhibited minor pain (score=1); and one cow in each group exhibited major pain (score=2). The average for the two groups remained very similar through grading period 4. At grading period 5, the average for the aluminum acetate group was slightly higher at 0.64, while the copper sulfate average was 0.45.

The last attribute was locomotion, as shown in Table 7 and FIG. 4, and measured on a scale of 1-5.

TABLE 7

Locomotion Score Distribution

| | Grading Period | | | | |
|---|---|---|---|---|---|
| Grade Score | 1 (Day 0) | 2 (Day 5) | 3 (Day 10) | 4 (Day 14) | 5 (Day 19) |
| Aluminum | | | | | |
| 1 | 6 | 2 | 4 | 7 | 8 |
| 2 | 4 | 7 | 8 | 3 | 2 |
| 3 | 1 | 2 | 0 | 1 | 0 |
| 4 | 1 | 0 | 0 | 0 | 1 |
| 5 | 0 | 0 | 0 | 0 | 0 |
| CuSO4 | | | | | |
| 1 | 5 | 3 | 3 | 8 | 8 |
| 2 | 4 | 5 | 7 | 2 | 1 |
| 3 | 1 | 2 | 1 | 0 | 1 |
| 4 | 1 | 0 | 0 | 0 | 1 |
| 5 | 0 | 0 | 0 | 0 | 0 |
| Average Al | 1.75 | 2.00 | 1.67 | 1.45 | 1.45 |
| Average CuSO4 | 1.82 | 1.90 | 1.82 | 1.20 | 1.55 |
| Sum Al | 12 | 11 | 12 | 11 | 11 |
| Sum CuSO4 | 11 | 10 | 11 | 10 | 11 |

Similar to the other attributes described above, the locomotion scores for the aluminum acetate treatment were similar to the scores for those treated with copper sulfate. The score distribution for grading period 1 illustrates that the majority of the cows in both groups had a score of 1 or 2 at day 0. Thus, at the start of the study, the lesions had not yet caused significant impact on gait and movement. In both groups, locomotion scores increased initially, correlating to decreased locomotion. However, over time, both treatments resulted in an improvement in locomotion.

An objective of the herd study was to compare the number of cows in each group that exhibited the following three results: an inactive lesion color score (i.e. score=4 or 5), minor or no lesion pain (i.e. score=0 or 1), and an unchanged or reduced score for lesion size. Table 8 illustrates the initial and final scoring for the cows in each group that met the above-listed criteria, and essentially had an inactivated lesion by the end of the herd study.

TABLE 8

Cows Meeting Criteria for Inactivated Lesions

| | Size | | Color | | Appearance | | Pain | | Locomotion | |
|---|---|---|---|---|---|---|---|---|---|---|
| Cow ID | Day 0 | Day 19 | Day 0 | Day 19 | Day 0 | Day 19 | Day 0 | Day 19 | Day 0 | Day 19 |
| Aluminum | | | | | | | | | | |
| 1131G | 2 | 1 | 1 | 4 | 2 | 4 | 2 | 1 | 2 | 1 |
| 1208G | 1 | 1 | 1 | 4 | 2 | 5 | 1 | 1 | 1 | 1 |
| 1212G | 1 | 1 | 1 | 5 | 1 | 4 | 1 | 0 | 4 | 1 |
| R982G | 1 | 1 | 1 | 4 | 1 | 3 | 1 | 0 | 1 | 1 |
| CuSO4 | | | | | | | | | | |
| 1222Y | 1 | 1 | 1 | 4 | 2 | 4 | 1 | 0 | 1 | 1 |
| 964Y | 1 | 1 | 3 | 5 | 2 | 5 | 1 | 0 | 2 | 1 |
| L1133Y | 2 | 1 | 2 | 5 | 3 | 5 | 1 | 0 | 1 | 1 |
| L982Y | 1 | 1 | 1 | 4 | 1 | 4 | 1 | 0 | 1 | 1 |

As illustrated above in Table 3, none of the lesions in either group completely disappeared within the grading period. However, some of the lesions were designated as being "inactivated" based on a color score of 4 or 5 (see Table 4). Specifically, four out of 11 cows in each group exhibited an inactivation of the lesion. All attributes for each of these eight cows (four from each group) are listed above in Table 8. The average lesion size score at day 19 for each of these cows is 1.00 for both groups.

In summary, the overall performance of the two treatments was comparable. Four out of 11 cows in each group showed inactivated lesions by the end of the grading period. The copper sulfate treatment appeared to promote inactivation of the lesions faster, although, in general, the aluminum acetate achieved comparable results by the last grading period.

As outlined above, in the herd study, treatment A was a solution having copper sulfate at approximately 4.0 weight percent, whereas treatment B was a solution having aluminum acetate at 0.56 weight percent. A significantly lower concentration of aluminum acetate was used, compared to the copper sulfate, yet comparable results in retarding lesion growth were observed. The herd study illustrates that using aluminum as a metal astringent, instead of copper, is more economical due to lower concentration levels, in addition to the environmental advantage of aluminum, compared to copper.

As discussed above, aluminum forms polynuclear or polymeric species in an aqueous solution, under specific conditions. At a pH of 4.1, the aluminum acetate (Burow's solution) used in the herd study most likely contained a mixture of polymeric and monomeric aluminum species. It is believed that the polyaluminum species are responsible, in part, for the performance of the aluminum acetate in treating the lesions.

Concentrates and Optional Components

In some embodiments, the aqueous solution is formed from one or more concentrates to be diluted with water near the time of use. The concentrate may be in the form of a solid powder, tablet, dispersion or liquid. The metal astringent concentrate may be used alone or in combination with other components. For example, the aqueous solution may be formed by a combination of two concentrates that are mixed together and diluted with water. In that case, a first concentrate may contain the metal astringent and a second concentrate may contain at least one component that enhances the delivery or performance of the metal astringent.

Examples of enhancing components include, but are not limited to, surfactants, skin conditioners, buffering agents, and antimicrobial agents, as discussed further below. The enhancing components selected for a particular application may depend, in part, on the mode of applying the aqueous solution, as discussed further below. In some cases it may be preferred to use a two concentrate system, if for example some of the materials do not have long-term compatibility when mixed together. Also, a two-concentrate system provides greater flexibility to use different formulations of enhancing components, as desired or as necessary. In preferred embodiments, the first concentrate of the metal astringent is highly concentrated such that the user is able to use small quantities to form the aqueous solution. In preferred embodiments, the first concentrate is a liquid for ease of use.

In some embodiments, the aqueous solution contains a surfactant, which enables the aqueous solution to wet and spread over the skin by reducing the surface tension of the aqueous composition. Antimicrobial surfactants may be used to achieve the reduced surface tension while also offering antimicrobial properties. Cationic, nonionic, and zwitterionic surfactants may be preferred over anionic surfactants since they are more likely to be compatible with the highly cationic astringent salts. A suitable concentration of the surfactant in the aqueous solution is between approximately 0.05 and 1.0 weight percent.

In some embodiments, the aqueous solution includes a thickener to increase viscosity and retain a greater quantity of liquid on the skin's surface. Thickeners, or thickening agents, may include, but are not limited to, cellulosic thickeners (such as hydroxyethylcellulose, xanthan gun, and carboxymethylcellulose), surfactant thickened systems, associative thickeners, clays and silicas. When a thickener is present, the composition may possess thixotropic properties of increased viscosity with decreasing shear. This may reduce misting effects with spraying or increase solution retention on the surface.

In some embodiments, the aqueous solution is thickened by a surfactant thickened system comprising a combination of surfactant components to impart rod-like micelle properties. Reference is made to U.S. Pat. No. 6,630,434, which is assigned to Ecolab Inc., the assignee of this application. In some embodiments, the surfactant thickened system uses a combination of a cationic surfactant and an anionic surfactant counterion to form rod micellar thickened compositions.

Cationic surfactants may include, but are not limited to, nitrogen containing amines, trialkylamines, amines having one or two alkyl groups and correspondingly two or one alkylene oxide groups, preferably ethylene oxide groups. Commonly available quaternary ammonium compounds can be used wherein the quaternary ammonium compound is made from aliphatic amines, aromatic amines or alkyl substituted aromatic amine substituents and trialkylamine oxides. Preferred quaternary ammonium surfactants include, but are not limited to, C12-18 alkyl trimethyl ammonium salts, C12-18 alkylpyridinium salts of chloride, bromide, iodide, sulfate, and methosulfate. Typical examples include, but are not limited to, myristyl trimethyl ammonium bromide, cetyl trimethyl ammonium chloride, cetylpyridinium chloride, stearyl trimethyl ammonium chloride, tallow trimethyl ammonium chloride, and mixtures thereof. Preferred amine oxide surfactants include C12-18 alkyl dimethyl amine oxides and N,N-bis(2-hydroxyethyl) C12-C18 alkyl amine oxides. Representative materials include, but are not limited to, lauryl dimethyl amine oxide, N,N-bis(2-hydroxyethyl) cocamine oxide, myristyl dimethyl amine oxide, cetyl dimethyl amine oxide, oleyl dimethyl amine oxide, stearyl dimethyl amine oxide, tallow dimethyl amine oxide, N,N-bis(2-hydroxyethyl) lauryl amine oxide, N,N-bis(2-hydroxyethyl) myristyl amine oxide, N,N-bis(2-hydroxyethyl) myristyl amine oxide, N,N-bis(2-hydroxyethyl) myristyl amine oxide, N,N-bis(2-hydroxyethyl) cetyl amine oxide, N,N-bis(2-hydroxyethyl) tallow amine oxide, and mixtures thereof. Preferred amine surfactants include, but are not limited to, C12-C18 alkyl dimethyl amines, N,N-bis(2-hydroxyethyl) C12-C18 alkyl amines, and N,N-bis(2-hydroxypropyl) C12-C18 alkyl amines. Typical examples include, but are not limited to, lauryl dimethyl amine, myristyl dimethyl amine, cetyl dimethyl amine, oleyl dimethyl amine, stearyl dimethyl amine, tallow dimethyl amine, N,N-bis(hydroxyethyl) myristyl amine, N,N-bis(hydroxyethyl) cetyl amine, N,N-bis(hydroxyethyl) oleyl amine, N,N-bis(hydroxypropyl) oleyl amine, N,N-bis(hydroxypropyl) tallow amine, and mixtures thereof.

The anionic surfactant counterions may include, but are not limited to, C1-C18 alkyl carboxylates, sulfates, and sulfonates. In preferred embodiments, the anionic surfactant counterions are C1-18 alkyl aryl carboxylates, sulfates, or sulfonates. Representative anionic surfactant counterions include, but are not limited to, salicylic acid, sodium cumene sulfonate, sodium toluene sulfonate, sodium xylene sulfonate, sodium dodecyl benzene sulfonate, sodium lauryl sulfate, sodium olefin sulfonate, and mixtures thereof.

The aqueous solution may also optionally comprise additional components configured to improve the performance of the metal astringent or to contribute additional functionality to the end product. For example, the composition may include skin conditioners, such as glycerin, propylene glycol, sorbitol, lanolin, derivates of polyethylene glycol (PEG)-lanolin and polypropylene glycol (PPG)-lanolin, aloe vera, and allantoin, to promote skin health and healing. Buffering agents may be used to adjust pH and control the speciation of the metal astringents. Buffers may include organic acids, such as monocarboxylates, phosophoric acid, carbonates, and similar products. The pH may be adjusted by adding alkalinity such as sodium bicarbonate, sodium carbonate, sodium hydroxide and potassium hydroxide. Film forming polymers may be used in the aqueous solution to hold residual active materials on the skin surface. The film forming polymers may include polyethylene glycol resins, polyvinyl alcohol, polyacrylates, polyvinyl pyrrolidinone, polyurethanes and corresponding copolymers.

The aqueous solution may also comprise antimicrobial agents such as quat based antimicrobials, phenolics, peracids, hydrogen peroxide, acidified sodium chlorite, hypochlorous acid, iodine, chlorhexidine, aldehyde-based germicides such as formaldehyde, glutaraldehyde, and fatty acids. Colorants selected from generally recognized dyes and pigments employed in food, drug and cosmetic formulations may be part of the composition. Organic astringents such as witch hazel, tannins and tea tree oil may be used as well. Any of these optional components may be used in various combinations depending on the desired features of a particular product.

As stated above, the aqueous solution may be formed by combining at least two concentrates together and diluting with water. A first concentrate may contain the metal astringent. A second concentrate may include at least one of the enhancing components described above. Alternatively, the enhancing components may be contained within more than one concentrate. For example, a second concentrate may contain a surfactant and/or a thickening agent, and a third concentrate may contain a skin conditioner and/or an antimicrobial agent. In some embodiments, the concentrates may be sold as a kit, which includes instructions for mixing the concentrates to form an aqueous solution with appropriate properties. As an example, the instructions may include instructions for forming a solution having a specific concentration of the metal and/or instructions to adjust a pH level of the aqueous solution to control speciation of the metal. In another example, the instructions may include instructions on forming a foam solution having a specific foam density.

Examples of Polyaluminum Speciation

As described above, in preferred embodiments, the metal astringent solution includes polymeric or polynuclear species of the metal. Appropriate ranges of the polymeric species were provided above. In preferred embodiments, the polymeric species in the aqueous solution is maximized to enhance the performance of the metal as an astringent. An aqueous solution containing the polymeric species may be formed from a polymeric concentrate, or by hydrolyzing a metal salt to form the polymeric species in situ.

An example of a commercially available polyaluminum concentrate is WCS 5051, which is aluminum chlorohydrate (12.4% active, as aluminum) and sold by Ecolab Inc., the assignee of this application. A study was conducted to determine if the polyaluminum concentrate remained stable over time when combined with other functional components, such as a surfactant and an antimicrobial (see Example 1 in Table 9 below). Specifically, the study compared the polymeric speciation of Example 1 to WCS 5051 after Example 1 was prepared and stored for seven weeks at 40 degrees Celsius. The pH of Example 1 was 4.6 and remained unchanged over the seven weeks.

TABLE 9

Composition of Example 1

| Component | Chemistry/Functionality | Weight percent |
|---|---|---|
| WCS 5051 (Ecolab) | Aluminum chlorohydrate - astringent | 9.92 |
| Glucopon DK 225 (Cognis) | Polyglucoside surfactant | 0.82 |
| Glutaraldehyde (50% active) | Antimicrobial | 0.22 |

As stated above, the aluminum content in the aluminum chlorohydrate was 12.4 weight percent. Since the weight percent of the aluminum chlorohydrate in Example 1 was 9.92 percent (i.e. diluted by approximately ten fold), the aluminum content in Example 1 was approximately 1.23 weight percent. As stated above, an appropriate range of the metal content in the aqueous solution is between approximately 0.01 and 1.5 weight percent.

The ferron assay procedure described in *Parker, Identification and Quantification of the $Al_{13}$ Tridecamer Polycation using Ferron* (referenced above), was followed to quantify the speciation of $Al_a$ (monomeric), $Al_b$ (mid-size polymeric), and $Al_c$ (large polymeric) in Example 1 after the seven week storage period. The percentages of $Al_a$ and $Al_b$ were based on the ferron absorbance after 3 minutes and 30 minutes, respectively. The large polymeric species ($Al_c$) was determined to be the difference between the total aluminum content and ($Al_a + Al_b$). The same procedure was repeated to quantify the speciation of WCS 5051. The results are shown in Table 10 below.

TABLE 10

| Aluminum Speciation Relative Percentages | | | |
| --- | --- | --- | --- |
|  | $Al_a$ | $Al_b$ | $Al_c$ |
| Example 1 | 9.7 | 3.9 | 86.4 |
| WCS 5051 | 11.6 | 2.3 | 86.1 |

The results from Table 10 show that the polyaluminum species of Example 1 remained physically stable and the solution maintained a similar speciation, compared to WCS 5051, after accelerated high temperature storage conditions. In Example 1, the polymeric species ($Al_b + Al_c$) was equal to 90.3 percent, whereas the polymeric species in WCS 5051 was equal to 88.4 percent. This study validates that, in some embodiments, the astringent solution may be formed from a polyaluminum concentrate. The solution may be formed just prior to application to the animal, or in advance as a ready-to-use product.

In another example (Example 2), a polyaluminum system was formed in situ by combining two parts (1:1). The first part was an aqueous composition containing 8.94 weight percent aluminum chloride hexahydrate, and the second part was an aqueous composition containing 0.55 weight percent glacier acetic acid and 0.11 weight percent sodium hydroxide (NaOH). When combined, the aluminum content in the aqueous solution of Example 2 was 0.5 weight percent and the pH was 4.88. The results of the ferron assay showed the speciation of Example 2 as $Al_a$=75.1, $Al_b$=3.0 and $Al_c$=21.9. Example 2 illustrates that, in some embodiments, the polyaluminum species may be formed by adding a source of alkalinity to an aluminum salt.

Applying the Metal Astringent on the Animal

The present invention includes any known application technique for delivering an aqueous solution to the lower leg and hoof of the animal. The applications include, but are not limited to, foot baths, foam, direct spraying, and propellant spray. In preferred embodiments, an automated system, as described further below, is used for applying the aqueous solution to the animals.

Foot baths are currently the most common application mode for treating hairy heel warts and other hoof related diseases. Cows are directed to walk through troughs containing the liquid treatment. A disadvantage of foot baths is that the liquid treatment may easily become contaminated due to organic waste from the cows. In some cases the foot bath may even become a vehicle for transferring bacteria to other cows. Foot baths thus may require frequent replenishment, as well as significant labor commitments in some cases. The aqueous solution of a metal astringent may be applied to the hooves of the animals using known foot bath systems. In preferred embodiments, the foot bath system is automated to reduce labor costs, as well as make it easier for frequent replenishment of the treatment solution.

As an alternative to a foot bath, the aqueous solution may be sprayed on the hooves. An advantage of a spray application is that a fresh treatment is applied to each cow, as compared to a foot bath application which may become contaminated over time. In some embodiments, a worker may individually spray each cow as the cow is on its way into or out of the milking parlor. Alternatively, an automated system may be used to spray the treatment onto the hooves.

When using a spray application, additional components may be included in the aqueous solution to enhance application of the solution onto the skin and hooves. In some embodiments, thickeners, as described above, may be used to retain a greater quantity of liquid per skin area. Surfactants, including those with antimicrobial agents, may be also used in combination with or as an alternative to thickeners. The surfactants reduce the surface tension of the aqueous composition on the skin and thus help the solution to wet and spread over the skin. The composition also may contain film forming polymers that dry to a second skin to help in holding the astringent agents to the skin or to provide a protective barrier to the skin.

In some embodiments, a thickener is used in a spray application to increase a viscosity of the aqueous solution. In preferred embodiments, the viscosity of the aqueous solution is equal to or greater than approximately 20 centipoise for spray applications. As described above, suitable thickeners may include polymeric thickeners, clays, silicas, and associative thickeners. Moreover, surfactant thickened systems, also described above, may preferably be used to form an aqueous solution having the desired viscosity for spraying the aqueous solution onto the hooves and lower legs of an animal.

A propellant spray also may be used to apply an aqueous solution to the hooves and lower leg area. The propellant spray typically requires the use of volatile propellants.

The aqueous solution described herein also may be applied as a foam. The foam may be applied in two ways. The foam may be dispensed into a trough and the cows may then walk through the foam, similar to a liquid foot bath. Alternatively, the foam may be applied directly to the hooves using any known foam dispensing technique.

In a foam application, two important parameters include the density of the foam (i.e. how much liquid per unit volume) and the stability of the foam (specifically, a drainage rate of the foam). In preferred embodiments, the foam is intrinsically viscous and allows greater foam stability. For foam applications, an appropriate viscocity range for the aqueous solution is between approximately 14 and 100 centipoise. Many of the same features that may be beneficial to a spray application may also be useful in a foam application. For example, surfactants and thickeners may both be used to improve foam properties.

In order to deliver an adequate amount of the astringent solution to the hoof and surrounding lower leg area, it is important that the foam have some minimum foam density. A suitable range of foam density is between approximately 0.05 and 0.5 g/mL. A preferred foam density is approximately 0.1 g/mL. Density of the foam may be controlled in part by the equipment used to generate the foam.

Viscosity and Foam Stability

Surfactants may be used to increase solution viscosity of the foam. A study was conducted to investigate a correlation between solution viscosity and foam stability (i.e. foam half-life). Seven different foam compositions, shown in Table 11 below, were tested. A Brookfield DVII+Viscometer was used to determine viscosity, and a 400 mL sample for each composition was measured in a 600 mL beaker using RVT spindle 1 at 100 rpms.

Each of the foams was generated using a generic hand pump foaming device. The foam density was essentially constant among the compositions at approximately 0.10 to 0.11 g/mL. The foam half-life was measured as the time required for half of the total liquid in the foam to drain to a bottom of a 50 mL graduated cylinder.

Table 11 below outlines the composition for each foam product A-G. In each of the products, a weight percent of at least one component of the product was varied between 0.1 percent and 2.0 percent. Thus, each of products A-G had five samples with weight percents equal to 0.1, 0.3, 0.5, 1.0 and 2.0. Foam half-life and viscosity were measured for each sample.

TABLE 11

Viscosity and Foam Stability - Product Compositions (Wt %)**

| | A | B | C | D | E | F | G |
|---|---|---|---|---|---|---|---|
| Aluminum Chlorohydrate* | 1.2 | 1.2 | 1.2 | 1.2 | 1.2 | 1.2 | 1.2 |
| Acusol 880 (polymeric mat'l) | — | — | — | 0.2 | 0.2 | var. | — |
| Acusol 882 (polymeric mat'l) | — | — | — | 0.2 | 0.2 | var. | — |
| Aculyn 44 (polymeric mat'l) | — | — | — | — | — | — | var. |
| Glucopon 225DK (surfactant) | var. | var. | — | var. | var. | var. | var. |
| BTC 835 (surfactant) | — | var. | — | — | var. | var. | — |
| Ammonyx LO (surfactant) | — | — | var. | — | — | — | — |
| Water | q.s. | q.s. | q.s. | q.s. | q.s. | q.s. | q.s. |

*Wt % reported as aluminum, formulated using WCS 5051.
**Wt % reported on an active component basis, not as the starting raw material wt %

As shown in Table 11, all of the products A-G contained aluminum chlorohydrate, also known as polyaluminum chloride, with an aluminum content of 1.2 wt %. All of the products also contained at least one surfactant. Glucopon 225DK (70% active) from Cognis is a polyglucoside surfactant. BTC 835 (50% active) from Stepan Company is an alkyldimethylbenzalkonium chloride that acts as an antimicrobial surfactant. Ammonyx LO (30% active) or lauryl dimethyl amine oxide (LDAO) is another type of surfactant, also from Stepan Company. Acusol 880 (33.5% active), Acusol 882 (17.5% active) and Aculyn 44 (35% active) are polymeric materials from Rohm & Haas.

Products A, B and C did not include any of the three polymeric materials. Product A had varying amounts of the surfactant Glucopon 225DK, while product B had varying amounts of both Glucopon 225DK and a second surfactant, BTC 835. Only one surfactant, Ammonyx LO, was present in product C. Tables 12 and 13 below show the foam half-life and viscosity results for products A, B and C.

TABLE 12

Foam Half-Life of Surfactant Compositions (min)

| | Wt % of varied formula component(s) | | | | |
|---|---|---|---|---|---|
| | 0.1% | 0.3% | 0.5% | 1.0% | 2.0% |
| Product A | 0.5 | 4.2 | 4.5 | 4.9 | 5.2 |
| Product B | 2.5 | 3.4 | 3.4 | 3.8 | 4.1 |
| Product C | 2.8 | 3.2 | 3.5 | 4.1 | 4.4 |

TABLE 13

Viscosity of Surfactant Compositions (centipoise)

| | Wt % of varied formula component(s) | | | | |
|---|---|---|---|---|---|
| | 0.1% | 0.3% | 0.5% | 1.0% | 2.0% |
| Product A | 11.1 | 11.3 | 11.4 | 11.6 | 11.8 |
| Product B | 11.1 | 11.3 | 11.6 | 11.8 | 12.1 |
| Product C | 11.3 | 11.6 | 11.9 | 12.6 | 12.4 |

Product B contained two different types of surfactants, but Product B had a shorter half-life compared to Product A with only one type of surfactant. Moreover, Products A and B exhibited similar viscosities. Product C, which contained a single surfactant (Ammonyx LO), showed similar foam half-life and viscosity results to Products A and B. In general, as the surfactant levels increased, Products A, B and C exhibited a small increase in viscosity. Foam half-life increased from less than 3 minutes to up to 4 or 5 minutes at the higher surfactant levels.

Product D had a variable amount of Gluocopon 225 DK and did not contain BTC 835. Product E had a variable amount of both Gluocopon 225 DK and BTC 835. Products D and E had constant amounts of polymeric materials Acusol 880 and 882.

TABLE 14

Foam Half-Life of Surfactant Compositions (min)

| | Wt % of varied formula component(s) [active] | | | | |
|---|---|---|---|---|---|
| | 0.1% | 0.3% | 0.5% | 1.0% | 2.0% |
| Product D | 8.8 | 9.4 | 10.2 | 10.8 | — |
| Product E | 7.1 | 6.5 | 5.9 | 6.8 | 7.1 |

TABLE 15

Viscosity of Surfactant Compositions (centipoise)

| | Wt % of varied formula component(s) [active] | | | | |
|---|---|---|---|---|---|
| | 0.1% | 0.3% | 0.5% | 1.0% | 2.0% |
| Product D | 17.3 | 18.7 | 19.9 | 18.2 | — |
| Product E | 15.7 | 14.7 | 14.5 | 15.1 | 15.9 |

Inclusion of the polymeric materials (Acusol 880 and 882) in Products D and E resulted in an increased foam-half life (i.e. a more stable foam) and increased viscosity, as compared to the surfactant only compositions (Products A, B and C). The results in Tables 14 and 15 show a correlation between increased foam half-life and increased viscosity of the foam.

Finally, in Products F and G both the surfactants and the polymeric materials were varied. Product F contained the same components as Product E, with the difference being that in Product F, the levels of Acusol 880 and 882 were also increased. Product G contained varying amounts of polymeric material Aculyn 44 and surfactant Glucopon 225DK.

TABLE 16

Foam Half-Life of Surfactant Compositions (min)

Wt % of varied formula component(s) [active]

|  | 0.1% | 0.3% | 0.5% | 1.0% | 2.0% |
|---|---|---|---|---|---|
| Product F | 4.1 | 8.8 | 15.0 | 31.0 | 44.0 |
| Product G | 1.0 | 6.7 | 13.5 | 21.5 | — |

TABLE 17

Viscosity of Surfactant Compositions (centipoise)

Wt % of varied formula component(s) [active]

|  | 0.1% | 0.3% | 0.5% | 1.0% | 2.0% |
|---|---|---|---|---|---|
| Product F | 12.5 | 18.7 | 31.2 | 66.7 | 89.8 |
| Product G | 11.2 | 13.6 | 23.1 | 94.4 | — |

Product F exhibited both a longer foam half-life and a higher viscosity, as compared to Product E, as well as Products A-D. Products F and G illustrate that increasing both the polymeric material and the surfactant results in an increased foam half-life. Products F and G also both showed a correlation between foam stability and foam viscosity.

In summary, the study of Products A-G illustrates that foam stability may increase with the use of surfactants, but the foam stability may plateau above a certain surfactant concentration. The addition of polymeric materials with the surfactant may be used to increase solution viscosity, which correlates to an increase in foam stability.

Another study was conducted with WCS 5051 (polyaluminum concentrate) to determine if a surfactant thickened system, as described above, results in an increased foam stability. The aqueous solution of Example 3 contained WCS 5051, Ammonyx CETAC, and Stepanate SXS (see Table 18 below). The pH of Example 3 was 4.6; as such, the speciation of the aluminum in Example 3 is most likely similar to the speciation shown in Table 10 above for Example 1. Viscosity of the aqueous solution was measured using spindle 2 of a Brookfield Viscometer at 100 rpms. Foam half-life was recorded as the time when half of the total liquid in the foam drained to the bottom of a graduated cylinder.

TABLE 18

Composition of Example 3

| Component | Weight Percent |
|---|---|
| WCS 5051 (Ecolab) | 9.74 |
| Ammonyx CETAC, 25% (Stepan) | 2.0 |
| Stepanate SXS, 40% (Stepan) | 0.6 |

The viscosity of Example 3 was 72 centipoise and the foam half-life was 9.5 minutes. Example 3 had a significantly higher viscosity compared to Products A-C (see Table 13 above). It is believed that the combination of Ammonyx CETAC and Stepanate SXS in Example 3 is responsible for the increased viscosity. More specifically, it is believed that the combination of Ammonyx and Stepanate resulted in a surfactant thickened system with rod-like micelle properties. The longer foam half-life of Example 3, compared to Products A-C (see Table 12 above), is due, in part, to the increased viscosity of the solution. The surfactant thickened systems described herein may be used in both foam and spray applications to achieve a desired viscosity.

Automated Systems

As stated above, the astringent solution described herein may be applied to the hooves and lower legs of the animal using any known application mode. Labor costs are a major concern to farmers. In preferred embodiments, an automated system is used to apply the solution, in order to reduce labor costs. The automated system may use a programmable time sequence and/or sensors that trigger dispensing. For example, in a foot bath application, whether a traditional liquid solution or a foam, a program may be used such that the treatment is dispensed into the trough at specific time intervals, and the old treatment solution is automatically drained before dispensing the replacement treatment solution. Instead of a time interval, the system may monitor a number of animals that have passed through the trough and automatically replenish the trough at a predetermined interval. Alternatively, sensors within the trough may be used to determine when the metal astringent falls below a predetermined concentration (due to contamination in the trough) and/or when waste levels in the trough reach a specific level. In a spray application, sensors may be used to determine a presence of an animal requiring treatment.

For dairy cows, it may be preferable to apply the treatment prior to entering a milking parlor. Milking parlors are generally kept very clean, thus providing adequate time for contact between the solution and the skin and the hoof before returning to a potentially soiled environment. Alternatively, the treatment may be applied as the cows exit the milking parlor such that the cows receive the treatment immediately prior to moving to a housing environment that may be very dirty. The composition may be applied periodically, such as every day, every other day, or once a week, depending on the risk factors.

In some embodiments, more than one application technique may be used in combination or multiple applications may be used. For example, two foot baths may be used in series. The first foot bath may contain a detergent solution to remove dirt and manure from the hooves; the second foot bath may contain the astringent solution. It is also recognized that a rotation of treatments may be used.

Although the present disclosure has focused on the use of metal astringent agents for preventing and treating hairy wart disease in dairy cows, it is recognized that hairy wart disease is a problem for a range of ungulates, and most notably sheep. The method and system described herein for dairy cows is applicable to any type of animal susceptible to hairy heel wart disease or similar types of hoof related diseases.

Although the present invention has been described with reference to preferred embodiments, workers skilled in the art will recognize that changes may be made in form and detail without departing from the spirit and scope of the invention.

The invention claimed is:

1. A method of treating hairy heel warts, the method comprising:
    (a) preparing an aqueous solution consisting of (i) a metal astringent wherein the metal is selected from the group consisting of at least one of iron and aluminum, and further wherein the metal astringent is a mixture of polymeric and monomeric species, and the polymeric species is greater than approximately 10 weight percent of the metal astringent in the aqueous solution, (ii) and at least one of a thickening agent, a surfactant, a skin conditioner, a buffering agent, a film forming polymer, and a colorant, and combinations thereof; and
    (b) applying the aqueous solution to a lower leg and hoof area of a cow to treat hairy heel wart disease.

2. The method of claim 1 wherein the aqueous solution is prepared by hydrolyzing a metal salt such that a portion of the metal salt forms a polymeric species.

3. The method of claim 1 wherein the aqueous solution has a pH between approximately 4.0 and 6.0.

4. The method of claim 1 wherein the metal astringent consists of at least one of aluminum chloride, aluminum sulfate, sodium aluminum sulfate, potassium aluminum sulfate, aluminum acetate, aluminum subacetate, aluminum lactate, ferric chloride, ferric sulfate, ferric subsulfate, polyaluminum chloride, polyaluminum sulfate, polyaluminum chlorosulfate, polyaluminum silicate sulfate, polyferric chloride, polyferric sulfate, and poly-alumino-ferric sulfate.

5. The method of claim 1 wherein the polymeric species ranges between about 25 and about 95 weight percent of the metal astringent in the aqueous solution.

6. A method of treating hairy heel warts, the method comprising:
(a) preparing an astringent solution by diluting a polymeric metal concentrate consisting of at least one of aluminum and iron, and at least one of a thickening agent, a surfactant, a skin conditioner, a buffering agent, a film forming polymer, and a colorant, and combinations thereof; and
(b) applying the astringent solution to a lower leg and hoof area of a cow to treat hairy heel warts.

7. The method of claim 6 wherein the polymeric metal concentrate consists of at least one of polyaluminum chloride, polyaluminum sulfate, polyaluminum chlorosulfate, polyaluminum silicate sulfate, polyferric chloride, polyferric sulfate, and poly-alumino-ferric sulfate.

8. The method of claim 6 wherein a metal content in the astringent solution has a concentration between approximately 0.01 and approximately 1.5 weight percent.

9. The method of claim 6 wherein the astringent solution consists of a mixture of polymeric and monomeric species, and the polymeric species ranges between approximately 25 and approximately 95 weight percent of the astringent solution.

10. The method of claim 6 wherein preparing the astringent solution includes diluting a second concentrate consisting of at least one of a thickening agent, a surfactant, a skin conditioner, a buffering agent, a film forming polymer, and a colorant, and combining the diluted polymeric metal concentrate and the diluted second concentrate to form the astringent solution.

11. A method of treating hairy heel warts, the method comprising:
(a) preparing an aqueous solution consisting of a metal astringent including at least one of iron and aluminum, and having a concentration in the aqueous solution that is therapeutically effective to treat hairy heel wart disease, and at least one of a thickening agent, a surfactant, a skin conditioner, a buffering agent, a film forming polymer, and a colorant, and combinations thereof; and
(b) spraying the aqueous solution onto a lower leg and hoof area of a cow, wherein a viscosity of the aqueous solution is greater than or equal to 20 centipoise.

12. The method of claim 11 wherein spraying the aqueous solution onto the lower leg and hoof area of the animal includes an automated device for dispensing the aqueous solution.

13. A method of treating hoof-related disease in animals, the method consisting of:
(a) preparing an aqueous solution consisting of a metal astringent including at least one of iron and aluminum, wherein the metal astringent is a mixture of polymeric and monomeric species, and the polymeric species is greater than approximately 10 weight percent of the metal astringent in the aqueous solution, and at least one of a thickening agent, a surfactant, a skin conditioner, a buffering agent, a film forming polymer, and a colorant, and combinations thereof; and
(b) applying the aqueous solution to a lower leg and hoof area of an animal to treat or prevent hoof-related disease.

14. The method of claim 13 wherein the aqueous solution is prepared by hydrolyzing a metal salt such that a portion of the metal salt forms a polymeric species.

15. The method of claim 13 wherein the aqueous solution has a pH between approximately 4.0 and 6.0.

16. The method of claim 13 wherein the metal astringent is selected from the group consisting of aluminum chloride, aluminum sulfate, sodium aluminum sulfate, potassium aluminum sulfate, aluminum acetate, aluminum subacetate, aluminum lactate, ferric chloride, ferric sulfate, ferric subsulfate, polyaluminum chloride, polyaluminum sulfate, polyaluminum chlorosulfate, polyaluminum silicate sulfate, polyferric chloride, polyferric sulfate, and poly-alumino-ferric sulfate, and combinations thereof.

17. The method of claim 13 wherein the polymeric species ranges between about 25 and about 95 weight percent of the metal astringent in the aqueous solution.

18. A method of treating hoof-related disease in animals, the method comprising:
(a) preparing an astringent solution consisting of diluting a polymeric metal concentrate including at least one of aluminum and iron; and
(b) applying the astringent solution to a lower leg and hoof area of an animal to treat and prevent hoof disease.

19. The method of claim 18 wherein the polymeric metal concentrate consists of at least one of polyaluminum chloride, polyaluminum sulfate, polyaluminum chlorosulfate, polyaluminum silicate sulfate, polyferric chloride, polyferric sulfate, and poly-alumino-ferric sulfate, and combinations thereof.

20. The method of claim 18 wherein a metal content in the astringent solution has a concentration between approximately 0.01 and approximately 1.5 weight percent.

21. The method of claim 18 wherein the astringent solution consists of a mixture of polymeric and monomeric species, and the polymeric species ranges between approximately 25 and approximately 95 weight percent of the astringent solution.

22. The method of claim 18 wherein preparing the astringent solution includes diluting a second concentrate consisting of at least one of a thickening agent, a surfactant, a skin conditioner, a buffering agent, a film forming polymer, and a colorant, and combining the diluted polymeric metal concentrate and the diluted second concentrate to form the astringent solution.

23. A method of treating hoof-related disease in animals, the method comprising:
(a) preparing an aqueous solution consisting of a metal astringent including at least one of iron and aluminum, and having a concentration in the aqueous solution that is therapeutically effective to treat and prevent hoof disease, and at least one of a thickening agent, a surfactant, a skin conditioner, a buffering agent, a film forming polymer, and a colorant, and combinations thereof; and
(b) spraying the aqueous solution onto a lower leg and hoof area of an animal, wherein a viscosity of the aqueous solution is greater than or equal to 20 centipoise.

24. The method of claim 23 wherein spraying the aqueous solution onto the lower leg and hoof area of the animal includes an automated device for dispensing the aqueous solution.

\* \* \* \* \*